(12) United States Patent
Cahill et al.

(10) Patent No.: US 7,842,026 B2
(45) Date of Patent: Nov. 30, 2010

(54) SYRINGE ACTIVATED-VALVE FOR FLUSHING A CATHETER AND METHODS THEREOF

(75) Inventors: Ryan Joseph Cahill, Brighton, MA (US); Stephanie M. Kladakis, Watertown, MA (US)

(73) Assignee: NMT Medical, Inc., Boston, MA (US)

( * ) Notice: Subject to any disclaimer, the term of this patent is extended or adjusted under 35 U.S.C. 154(b) by 0 days.

(21) Appl. No.: 11/646,847

(22) Filed: Dec. 28, 2006

(65) Prior Publication Data

US 2007/0179474 A1   Aug. 2, 2007

Related U.S. Application Data

(60) Provisional application No. 60/754,766, filed on Dec. 29, 2005.

(51) Int. Cl.
*A61M 39/00* (2006.01)
*A61M 39/10* (2006.01)
*A61M 25/00* (2006.01)
*A61M 25/18* (2006.01)
*A61M 25/16* (2006.01)

(52) U.S. Cl. .......... 604/533; 604/523; 604/264

(58) Field of Classification Search ........ 604/533, 604/523, 264, 249; 137/843
See application file for complete search history.

(56) References Cited

U.S. PATENT DOCUMENTS

| 3,344,785 | A | * | 10/1967 | Hamilton | 604/6.1 |
| 3,831,629 | A | * | 8/1974 | Mackal et al. | 137/843 |
| 4,133,314 | A | * | 1/1979 | Bloom et al. | 604/405 |
| 4,946,440 | A | * | 8/1990 | Hall | 604/164.09 |
| 5,059,186 | A | * | 10/1991 | Yamamoto et al. | 604/537 |
| 5,360,413 | A | * | 11/1994 | Leason et al. | 604/249 |

(Continued)

FOREIGN PATENT DOCUMENTS

BE   898 705   5/1984

(Continued)

OTHER PUBLICATIONS

Halkey-Roberts Medical Valves & Components Catalog (3 pages).

(Continued)

*Primary Examiner*—Kevin C. Sirmons
*Assistant Examiner*—Michael J Anderson
(74) *Attorney, Agent, or Firm*—Finnegan, Henderson, Farabow, Garrett & Dunner, L.L.P.

(57) ABSTRACT

This invention relates to a syringe-activated valve for flushing a catheter for delivering an implant to an anatomical site, such as a patent foramen ovale in a patient and method thereof. In one embodiment, a catheter includes a proximal end, a distal end, a "Y" connector at the proximal end, the "Y" connector having a guide wire port and a connector port, a syringe activated valve having a first end and a second end, the second end of syringe-activated valve connecting to the connector port of the "Y" connector, and a syringe connecting to the first end of the syringe-activated valve. Saline is injected by the syringe through the syringe-activated valve into the proximal end of the catheter, thereby flushing air from the catheter lumen out of the distal end of the catheter.

11 Claims, 5 Drawing Sheets

U.S. PATENT DOCUMENTS

| | | | | |
|---|---|---|---|---|
| 5,465,938 A * | 11/1995 | Werge et al. | ............. | 251/149.1 |
| 5,531,672 A * | 7/1996 | Lynn | ......................... | 604/6.12 |
| 5,535,785 A * | 7/1996 | Werge et al. | ................. | 137/843 |
| 5,549,569 A * | 8/1996 | Lynn et al. | .................. | 604/191 |
| 5,573,516 A * | 11/1996 | Tyner | .......................... | 604/249 |
| 5,584,808 A * | 12/1996 | Healy | ........................... | 604/86 |
| 5,743,894 A * | 4/1998 | Swisher | ...................... | 604/320 |
| 5,749,861 A * | 5/1998 | Guala et al. | ................. | 604/249 |
| 5,810,835 A * | 9/1998 | Ryan et al. | .................. | 606/108 |
| 5,833,213 A * | 11/1998 | Ryan | ........................ | 251/149.1 |
| 5,967,490 A | 10/1999 | Pike | ........................ | 251/149.1 |
| 6,030,369 A * | 2/2000 | Engelson et al. | ............ | 604/264 |
| 6,158,458 A * | 12/2000 | Ryan | ........................ | 137/515.5 |
| 6,245,048 B1 * | 6/2001 | Fangrow et al. | ............ | 604/249 |
| 6,695,817 B1 * | 2/2004 | Fangrow, Jr. | .......... | 604/167.01 |
| 6,706,022 B1 | 3/2004 | Leinsing et al. | ............. | 604/247 |
| 6,802,490 B2 | 10/2004 | Leinsing et al. | .......... | 251/149.6 |
| 6,871,838 B2 * | 3/2005 | Raines et al. | ............ | 251/149.4 |
| 6,916,309 B2 * | 7/2005 | Fangrow, Jr. | ........... | 604/167.01 |
| 6,932,795 B2 * | 8/2005 | Lopez et al. | ................. | 604/249 |
| 7,008,404 B2 * | 3/2006 | Nakajima | ................... | 604/158 |
| 7,033,339 B1 * | 4/2006 | Lynn | .......................... | 604/256 |
| 7,094,218 B2 * | 8/2006 | Rome et al. | ............... | 604/99.04 |
| 7,104,520 B2 | 9/2006 | Leinsing et al. | .......... | 251/149.6 |
| RE39,334 E | 10/2006 | Lynn | .......................... | 604/533 |
| 7,114,701 B2 * | 10/2006 | Peppel | ........................ | 251/149 |
| 7,226,433 B2 * | 6/2007 | Bonnette et al. | ........ | 604/164.01 |
| 2002/0002352 A1 * | 1/2002 | Becker et al. | ............... | 604/249 |
| 2003/0141477 A1 | 7/2003 | Miller | ...................... | 251/149.1 |
| 2004/0006330 A1 | 1/2004 | Fangrow, Jr. | ................. | 604/533 |
| 2004/0249349 A1 * | 12/2004 | Wentling | ..................... | 604/248 |
| 2005/0192546 A1 * | 9/2005 | Griego et al. | ............... | 604/264 |
| 2006/0027270 A1 * | 2/2006 | Truitt et al. | ................... | 137/843 |
| 2006/0037618 A1 * | 2/2006 | Halbert | .................. | 128/207.16 |
| 2006/0135948 A1 * | 6/2006 | Varma | ........................ | 604/523 |
| 2007/0021721 A1 * | 1/2007 | Lopez | ........................ | 604/249 |
| 2007/0106229 A1 * | 5/2007 | Wong | .......................... | 604/249 |
| 2007/0246674 A1 * | 10/2007 | Kiehne | .................... | 251/149.6 |

FOREIGN PATENT DOCUMENTS

| | | |
|---|---|---|
| EP | 0 471 547 | 2/1992 |
| WO | WO 96/39997 | 12/1996 |

OTHER PUBLICATIONS

US 6,971,630, 12/2005, Leinsing et al. (withdrawn)

* cited by examiner

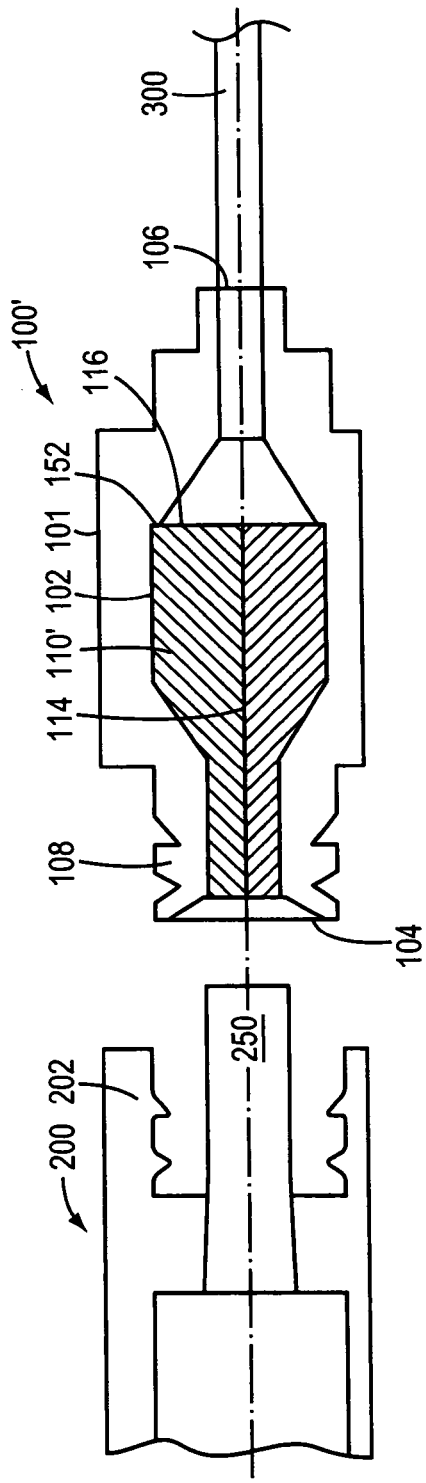
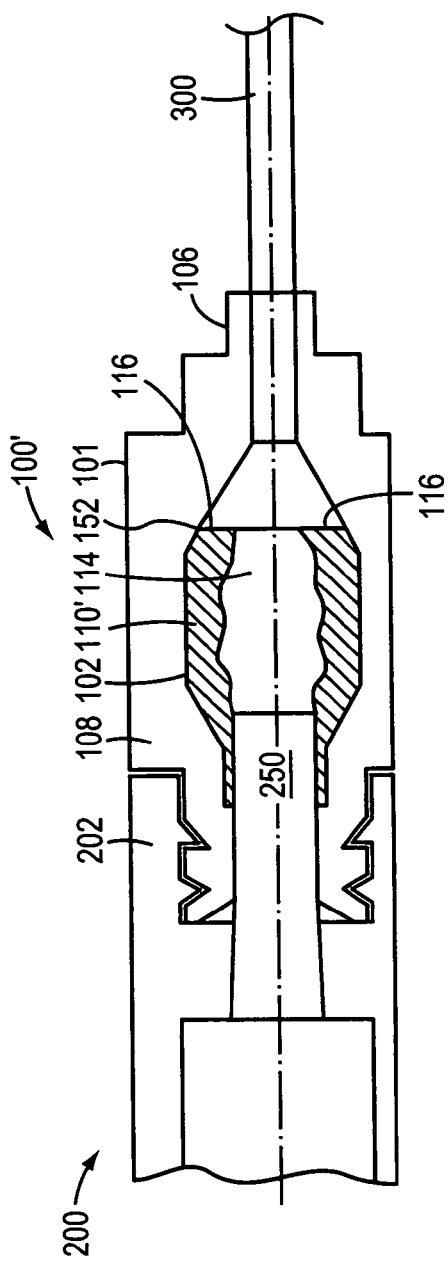
FIG. 4
FIG. 5

SYRINGE ACTIVATED-VALVE FOR FLUSHING A CATHETER AND METHODS THEREOF

RELATED APPLICATIONS

This application claims priority to and benefit of U.S. provisional application No. 60/754,766 the entire content of which is incorporated by reference herein.

FIELD OF INVENTION

The invention relates to a delivery system including an intravascular catheter and a syringe activated valve for delivering an implant, a method of flushing an intravascular delivery catheter, and specifically to the use of a syringe activated valve in flushing air bubbles out of the delivery catheter.

BACKGROUND OF THE INVENTION

An intravascular catheter is typically used to introduce an implant, e.g., an intracardiac occluder, into a patient's body. Generally, an intravascular catheter is an elongate tube having an elongate lumen extending from the proximal to the distal end of the catheter. Before a delivery catheter is introduced into the patient's body, air trapped in the catheter must be removed. To do so, doctors typically inject saline to flush the catheter. Most commonly, saline is introduced by a syringe into the delivery catheter at its proximal end, and saline is flushed out of the distal end of the catheter. As the saline passes from proximal to distal through the catheter, the air bubbles are flushed from the catheter lumen and pushed out of the distal end of the catheter.

A catheter flushing port is usually an integrated part of the delivery catheter. The flushing port is typically one port of a Y-shaped connector at the proximal end of the delivery catheter. A typical catheter flushing mechanism includes a syringe for introducing saline, and a three-way stopcock for connecting the syringe to the flushing port of the "Y" connector thereby creating a liquid flow-path from the proximal end to the distal end of the catheter for the saline. A second port of the "Y" connector allows a delivery wire such as a guide wire to slide through the catheter.

FIG. 1 illustrates a typical form of a catheter flushing system 10 known to the prior art. It is used to remove air trapped in the catheter before the catheter is introduced into a patient's body. In this form, a delivery wire 302 slides through the guide wire port 308 of a "Y" connector 320. A syringe 200 for introducing saline is connected by a three-way stopcock 306 to the connector port 310 of the "Y" connector 320. The three-way stopcock 306 opens to create a liquid flow-path for the saline. Connections between the syringe 304 and the three-way stopcock 306 and between the three-way stopcock 306 and the "Y" connector 320 are standard luer locks. To flush the catheter, the three-way stopcock 306 is manually switched to open the flow path for saline between the syringe 200 and the connector port of the "Y" connector 320. The operation of the stopcock requires that the clinician hold the syringe, actuate the three-way stopcock to open the flow path and inject the saline to remove air in the delivery catheter. The clinician must then close the stopcock, remove the syringe and introduce the catheter into the patient, e.g., into the femoral artery. As a result, the simple act of flushing the delivery catheter is technically difficult.

The present invention addresses this difficulty.

SUMMARY OF THE INVENTION

In one aspect, this invention relates to a delivery system for delivering an implant such as a septal occluder to an anatomical site, for example, a patent foramen ovale (PFO) in a patient's body. The delivery system includes an intravascular catheter having a connector, a syringe activated valve joined to the connector and a port for introducing the implant into the intravascular catheter for delivery to the anatomical site in the patient. In one embodiment according to the invention, the syringe-activated valve is permanently and irreversibly joined to the connector.

In one embodiment of the invention the syringe-activated valve is permanently joined to a Y-connector. The syringe-activated valve may be a slit-type, compression, or stopper valve, for example.

In one embodiment of the invention, the syringe-activated valve has a valve housing including a proximal end, a distal end, and an axial bore including a proximal cylindrical bore, a distal cylindrical bore, and a shoulder positioned between the proximal cylindrical bore and the distal cylindrical bore. In a particular embodiment, the syringe-activated valve further includes a sealing member enclosed by the valve housing. The sealing member is slideably and axially disposed in the axial bore and is compressible between a relaxed state and a compressed state. As the sealing member is compressed the valve transitions between an open position and a closed position.

The sealing member includes a proximal portion, a distal portion, and an intermediate portion. The intermediate portion of the sealing member has a shoulder that interfaces with and cooperates with the shoulder of the valve housing when the valve is in the closed position. In one embodiment, the syringe-activated valve further features a backstop positioned in the distal bore of the valve housing distal to the distal portion of the sealing member and proximal to the distal end of the valve housing, wherein the sealing member occludes the axial bore in the closed position and opens the axial bore in the open position.

In one embodiment of the invention, the backstop is disc shaped and has at least one perforation that extends from the proximal face through the distal face of the backstop. Alternatively, the backstop has at least one gap positioned between the backstop and the wall of the distal axial bore. In yet another embodiment of the invention, the backstop may have a combination of one or more perforations and one or more gaps.

The backstop may feature one or more projections on the proximal face. In one embodiment, the backstop features a cross-shaped projection that extends proximally from the proximal face.

In another aspect, the invention relates to a method for flushing a catheter for delivery of an implant to an anatomical site in a patient. The delivery catheter may be used to deliver, for example, an intracardiac occluder to seal, for example, a patent foramen ovale (PFO) in a patient. In one embodiment, a catheter is provided, including a lumen, a proximal end, a distal end, a "Y" connector at the proximal end, the "Y" connector comprising a connector port and a guide wire port, and a syringe-activated valve comprising a first end and a second end, the second end of the syringe-activated valve connected to the connector port of the "Y" connector. Saline is injected by the syringe through the syringe-activated valve at the connector port into the proximal end of the catheter, thereby flushing air from the catheter lumen out of the distal end of the catheter.

BRIEF DESCRIPTION OF THE DRAWINGS

FIG. 4 illustrates a cross section of a valve including a compressible member according to another embodiment of the invention;

FIG. 5 illustrates a cross section of the valve illustrated in FIG. 4, connected at one end to a syringe according to an embodiment of the invention;

DETAILED DESCRIPTION OF THE PREFERRED EMBODIMENTS

The present invention will be more completely understood through the following detailed description, which should be read in conjunction with the attached drawings. In this description, like numbers refer to similar elements within various embodiments of the present invention. Within this detailed description, the claimed invention will be explained with respect to preferred embodiments. However, the skilled artisan will readily appreciate that the methods and systems described herein are merely exemplary and that variations can be made without departing from the spirit and scope of the invention.

Specific embodiments of a syringe-activated valve 100 including, for example, a slit-type valve 100, a compression valve 100', and a stopper valve 100' and methods of their use for percutaneous transvascular delivery of an implant to an anatomical site in a patient's body according to the invention are described below As used herein, the term proximal means closer to the operator while the term distal means further away from the operator than proximal.

As used herein, the term syringe-activated means the engagement and disengagement of a syringe with the valve to reversibly activate the valve from a closed valve position in which a fluid or a gas can not cross the valve, to an open valve position in which a fluid or a gas can cross the valve.

In one aspect, the invention relates to a valve used with an intravascular catheter that delivers an implant to an anatomical site in a patient's body. For example, the valve and intravascular catheter may be used to deliver an intracardiac septal occluder via a percutaneous, transvascular route to a patent foramen ovale in a patient's body.

Figure 1:
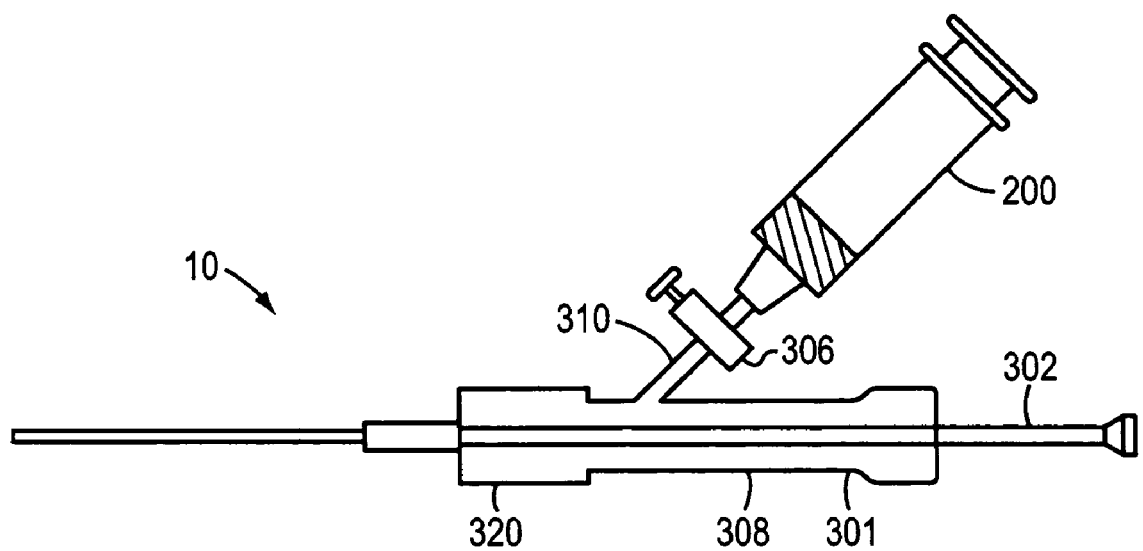
FIG. 1 illustrates a typical catheter flushing system known to the prior art.
Figure 2:
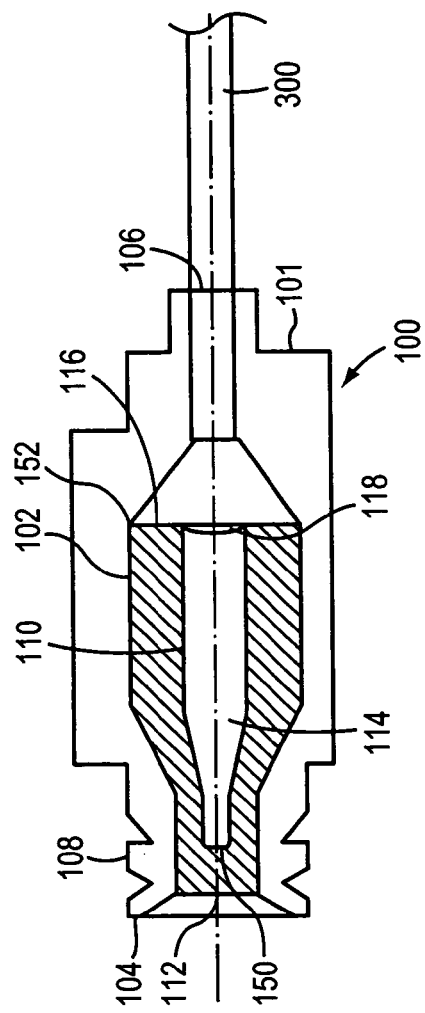
FIG. 2 illustrates a cross-section of a slit-type valve according to an embodiment of the present invention.

FIG. 2 illustrates a valve 100 used in an embodiment of the present invention. The exemplary valve 100 is a slit-type valve including a housing 101 defining a central axial bore 102, and having a first open end 104 and a second open end 106. The first open end 104 is designed to receive the tip 250 of a syringe 200 discussed below in greater detail with respect to FIG. 3. In one embodiment of the slit-type valve 100, the first open end 104 has, for example, a female luer lock connector 108 that mates with and locks on to a corresponding male luer connector 202 of the syringe tip 250 discussed below with respect to FIG. 3. The second open end 106 of the slit-type valve 100 connects with a connecting member (not shown) such as a female connector, or a male connector at the proximal end of a fluid line of the delivery catheter 300.

With continued reference to FIG. 2, the valve housing 101 encloses a substantially cylindrical sealing member 110 constructed of silicone or some other resilient elastomeric material such as, for example, rubber. Alternatively, the sealing member 110 has another shape such as a ring, or a partial ring, for example. In another embodiment according to the invention, the sealing member 110 is activated by a spring mechanism located between the member and the valve housing 101. The sealing member 110 forms a central axial fluid passageway 114 extending from a first open end 104 to a second open end 106. The proximal end 150 of the sealing member 110 includes a slit 112. The slit 112 extends entirely through the proximal end 150 of the sealing member 110 from the first open end 104 into the passageway 114. The slit 112 in its relaxed, uncompressed position is closed thereby preventing passage of fluid or gas from the outside of the valve 100 into the passageway 114. The distal end 152 of the sealing member 110 terminates, in one embodiment, at a flat end 116 of the inner wall of the housing 101 aligned substantially perpendicular to the long axis of the passageway 114. The distal end 152 of the sealing member 110 has an opening 118 in fluid communication with the lumen of the catheter 300. In one embodiment, the proximal end of the catheter 300 is joined via a Y-connector, or alternatively, directly to the housing 101 of the valve 100 by a friction fit joint, luer lock, adhesive, or other mechanisms known in the art for joining a catheter to a valve. The opening 118 at the second end of the sealing member 110 aligns the passageway 114 of the valve body with the lumen of the catheter 300 providing a fluid flow path between the fluid passageway 114 in the sealing member 110 and the lumen of the delivery catheter 300.

Figure 3:
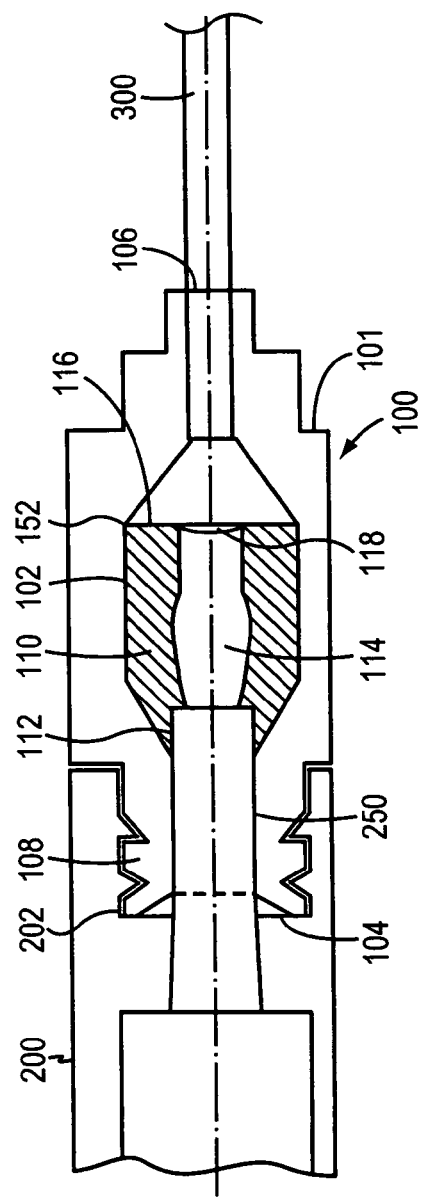
FIG. 3 illustrates the cross-section of the slit-type valve shown in FIG. 2, connected at one end to a syringe by a luer lock according to an embodiment of the invention.

FIG. 3 illustrates a change in the shape of the sealing member 110 of the valve 100 when the first open end 104 of the valve 100 is engaged by, for example, the luer connector 202 of the syringe 200. The sealing member 110 functions as a seal around the tip 250 of the syringe 200. As the tip 250 of the syringe 200 is introduced into the proximal end 150 of the sealing member 110, the otherwise closed slit 112 at the proximal end 150 of the sealing member 110 parts thereby opening a fluid communication from the lumen of the syringe 200 to the passageway 114 inside the sealing member 110. The open fluid communication permits a liquid, for example, saline, to flow from the syringe 200 through the valve 100 to the lumen of the delivery catheter 300 connected to the distal end of the valve 106. When the syringe 200 is disengaged from the valve 100, the slit 112 of the sealing member 110 returns to its relaxed closed position thereby sealing the passageway 114 at the first open end 104 of the valve 100. In other words, the closed slit 112 prevents fluid or gas from moving across the first open end 104 of the valve 100 from the passageway 114 to outside of the valve 100 and in the reverse direction from outside of the valve 100 into the passageway 114.

FIG. 4 illustrates yet another valve according to an embodiment of the invention. The exemplary valve 100' is a compression valve including a housing 101 defining a central axial bore 102 (best viewed in FIG. 5), and having a first open end 104 and a second open end 106. The first open end 104 is designed to receive the tip 250 of a syringe 200 discussed below in greater detail with respect to FIG. 5. In one embodiment of the compression valve 100', the first open end 104 has, for example, a female luer lock connector 108 that mates with and locks on to a corresponding male luer connector 202 discussed below with respect to FIG. 5 of the syringe tip 250. The second open end 106 of the compression valve 100' connects directly to or alternatively via a connecting member (not shown) at the proximal end of a fluid line of the delivery catheter 300.

With continued reference to FIG. 4, the valve housing 101 encloses a substantially elongated cylindrical sealing member 110' constructed of silicone or some other resilient elastomeric material such as, for example, rubber. The sealing member 110' forms a central axial fluid passageway 114 extending from a first open end 104 to a second open end 106. The central axial fluid passageway 114 is biased to a closed position when the resilient sealing member 110' is in a relaxed, uncompressed state as further described below.

Referring still to FIG. 4, the sealing member 110' in its relaxed, uncompressed state occludes the passageway 114 thereby preventing passage of fluid or gas from the outside of the valve 100 into the passageway 114. The distal end 152 of the sealing member 110' terminates, in one embodiment, at a flat end 116 of the inner wall of the housing 101 aligned substantially perpendicular to the long axis of the passageway 114. The distal end 152 of the sealing member 110' has an opening 118 in fluid communication with the lumen of the catheter 300. The proximal end of the catheter 300 is joined by a connector (not shown) or alternatively directly to the housing 101 of the valve 100 by a friction fit joint, luer lock, adhesive, or other mechanisms known in the art for joining a catheter to a valve. The opening 118 at the second end of the sealing member 110' aligns the passageway 114 of the valve body with the lumen of the catheter 300 providing a fluid flow path between the fluid passageway 114 in the sealing member 110' and the lumen of the delivery catheter 300.

FIG. 5 illustrates a change in the shape of the sealing member 110' of the compression valve 100 when the first open end 104 of the valve 100 is engaged by, for example, the luer connector 202 of the syringe 200. The sealing member 110' functions as a seal around the tip 250 of the syringe 200. As the tip 250 of the syringe 200 is introduced into the proximal end 150 of the sealing member 110', the otherwise relaxed conformation of the elongated sealing member 110' at the proximal end 150 of the sealing member 110' is compressed causing the sealing member 110' to be compressed against the inner wall of the valve housing 101. As the sealing member 110' is compressed the passageway 114 opens, as illustrated in FIG. 5, thereby introducing a fluid communication from the lumen of the syringe 200 to the passageway 114 inside the compressed sealing member 110'. The open fluid communication permits a gas, or liquid, for example, saline, to flow from the syringe 200 through the valve 100' to the lumen of the delivery catheter 300 connected to the distal end 106 of the valve. When the syringe 200 is disengaged from the valve 100', the sealing member 110' returns to its relaxed closed position thereby sealing the passageway 114 of the valve 100.

Figure 6:
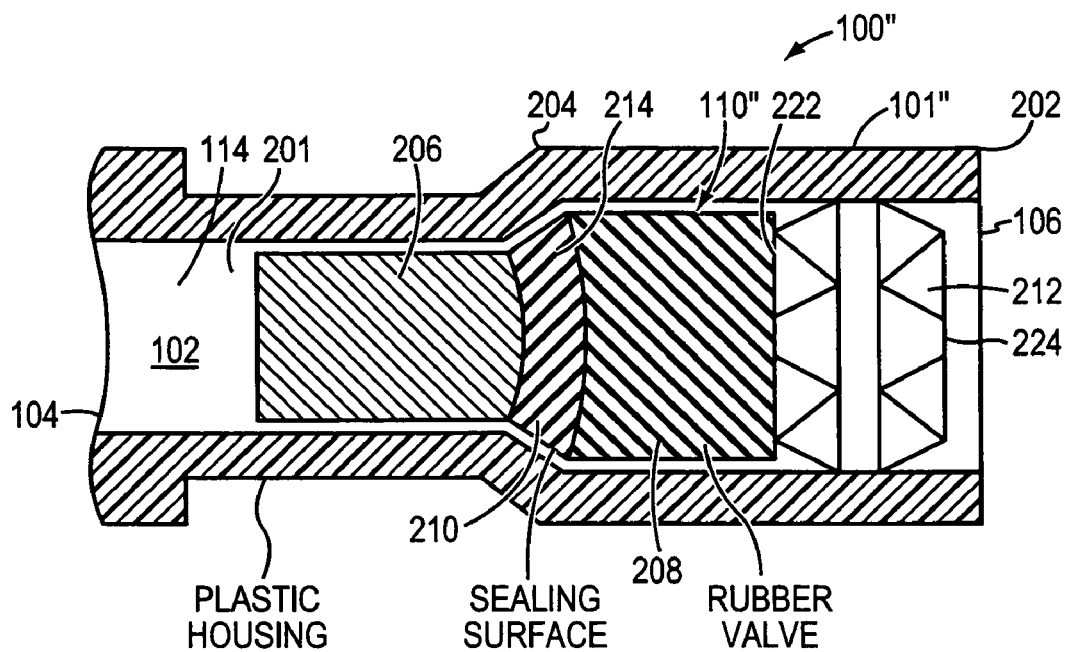
FIG. 6 illustrates a cross section of a stopper valve according to an embodiment of the present invention.

FIG. 6 illustrates yet another valve according to an embodiment of the invention. The valve 100" is a stopper valve including a housing 101". The housing 101" defines a central axial bore 102 having a first open end 104 and a second open end 106. The central axial bore 102 of the valve housing 101" includes a proximal cylindrical portion 201 and a distal cylindrical portion 202. In one embodiment according to the invention, the diameter of the proximal cylindrical portion 201 is narrower than the diameter of the distal cylindrical portion 202. The proximal cylindrical portion 201 and the distal cylindrical portion 202 of the central axial bore 102 interface at a shoulder 204 having a slope. In one embodiment, the shoulder 204 extends around the circumference of the valve housing 110" where the proximal cylindrical bore 201 and the distal cylindrical bore 202 interface as illustrated in FIG. 6.

With continued reference to FIG. 6, the first open end 104 receives the tip 250 of a syringe 200 discussed below in greater detail with respect to FIG. 8. In one embodiment of the stopper valve 100", the first open end 104 has, for example, a female luer lock connector (not shown) that mates with and locks on to a corresponding male luer connector 202 (not shown) discussed below with respect to the syringe tip illustrated in FIG. 8. The second open end 106 of the stopper valve 100" connects with a connecting member (not shown) at the proximal end of a fluid line of the delivery catheter 300 or, alternatively, directly to the fluid line of the catheter 300.

With continued reference to FIG. 6, the valve housing 101" encloses a sealing member 110" constructed of silicone or some other resilient elastomeric material such as, for example, rubber. The sealing member 110" is shaped much like a bottle stopper and is axially and slideably moveable in the central axial bore 102 of the valve 100". The sealing member 110" includes a substantially cylindrical proximal portion 206, a substantially cylindrical distal portion 208 and an intermediate portion 210 that is positioned between and joins the proximal portion 206 of the sealing member 110" to the distal portion 208 of the sealing member 110". The intermediate portion 210 forms a sealing member shoulder 214 which corresponds to and cooperates with the slope of the shoulder 204 of the valve housing 101".

In one embodiment of the sealing member 110", one or more of the proximal portion 206, intermediate portion 210 and distal portion 208 are hollow. In another embodiment of the invention, one or more of the proximal portion 206 and the distal portion 208 includes at least one slit (not shown) paralleling the long axis of the sealing member 110". The at least one slit may extend along a portion of or, alternatively, the entire length of the proximal portion 206 or the distal portion 208 of the sealing member 110". In one embodiment, one or more slits extend the entire length of the proximal 206 or distal portion 208 while at least one other slit extends along only a portion of the proximal 206 or distal portion 208 of the sealing member.

With continued reference to FIG. 6, the stopper valve 100" further includes a sealing member backstop 212. The backstop 212 is located in the distal cylindrical portion 202 of the axial bore 102 distal to the distal portion 208 of the sealing member 110" and proximal to the distal end 106 of the valve 100". In one embodiment, the backstop 212 is made from materials that are stiffer, i.e., less resilient than the materials that are used to make the sealing member 110". For example, the backstop 212 is made from materials such as polyethylene, or polypropylene, for example. In an alternative embodiment, the backstop 212 is made from the same materials as the sealing member 110".

Figure 7:
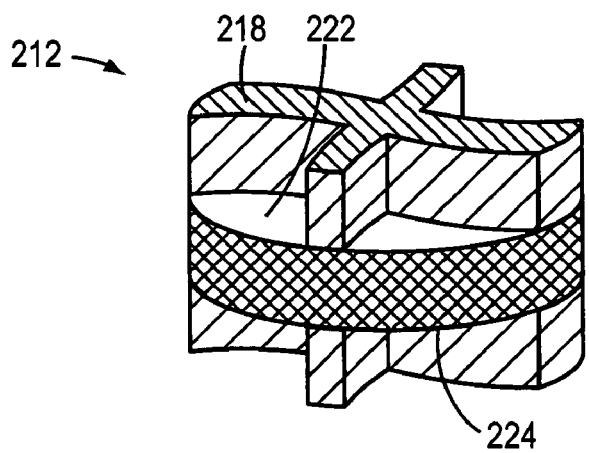
FIG. 7 illustrates a perspective side view of a sealing member backstop according to one embodiment of the invention.

Referring to FIG. 7, in one embodiment the backstop 212 is substantially disc shaped and includes a proximal face 222 and a distal face 224. Typically, the disc backstop 212 has the same diameter as the distal portion 208 of the sealing member 110". Alternatively, the width of the backstop 212 is narrower than the diameter of the distal portion 208 of the sealing member 110". In one embodiment of the invention, the backstop 212 includes at least one projection 218, for example, a cross shaped projection 218, illustrated in FIG. 7, extending outwardly from at least one of the proximal and distal face of the backstop 212. Alternatively, the at least one projection is cone shaped, rectangular, cylindrical, or pyramidal, for example. In one embodiment, one or more projections on the backstop is in alignment with one or more slits in the sealing member. With this alignment, the sealing member more readily compresses from proximal to distal. The backstop 212 further includes one or more perforations (not shown) through the backstop 212 from the proximal to the distal face and or one or more gaps (not shown) between the inner wall of the valve housing 101" and the backstop 212 to permit fluid communication between the distal cylindrical bore 202 that is proximal to the backstop 212 and the distal cylindrical bore 202 that is distal to the backstop 212.

Referring still to FIG. 7, the shoulder 214 of the sealing member 110" in its relaxed, uncompressed state interfaces with the shoulder 204 of the valve housing 101" thereby occluding the fluid passageway 114 much like a stopper inserted into the neck of a bottle.

Figure 8:
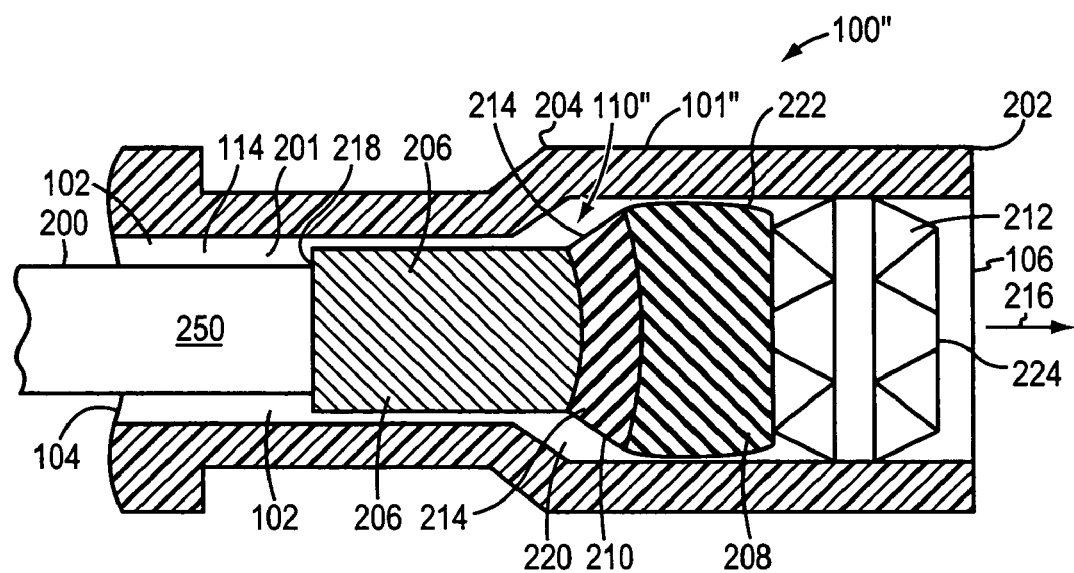
FIG. 8 illustrates a cross section of the valve illustrated in FIG. 6, connected at one end to a syringe according to an embodiment of the invention.

Referring now to FIG. 8, as a syringe 200 is inserted into the proximal cylindrical portion 201 of the central axial bore 102, the tip 250 of the syringe 200 abuts the proximal end 218 of the proximal cylindrical portion 206 of the sealing member 110". As the syringe is advanced distally in the direction of arrow 216, the distal end of the distal cylindrical portion 208 of the sealing member 110" is compressed against the proximal face 222 of the backstop 212. Simultaneously, the shoulder 214 of the intermediate portion 210 moves distally away from the shoulder 204 of the valve housing 101" leaving a gap 220 between the shoulder 214 of the intermediate portion 210 of the sealing member 110" and the shoulder 204 of the valve housing 101". With the sealing member 110" in the "gapped", i.e., open position, the passageway 114 is opened, as illustrated in FIG. 8, thereby introducing a fluid communication from the lumen of the syringe 200 through the proximal cylindrical bore 201, the gap 220, the distal cylindrical bore 202, and around or through the backstop 212. The open fluid communication permits a liquid, for example, saline, to flow from the syringe 200 through the valve 100" to the lumen of the delivery catheter 300 connected to the distal end of the valve 106. When the syringe 200 is disengaged from the valve 100", the sealing member 110" returns to its relaxed closed position in which the shoulder of the sealing member 110" interfaces with and cooperates with the shoulder of the valve housing 101" thereby sealing the passageway 114 of the valve 100".

Figure 9:
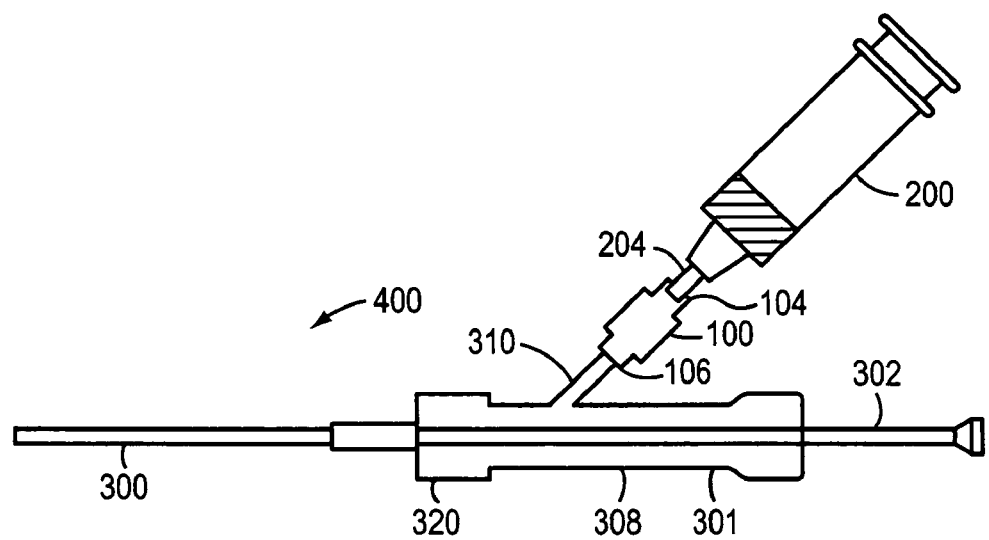
FIG. 9 illustrates a catheter flushing system including a valve according to an embodiment of the present invention.

FIG. 9 illustrates a delivery system 400 for delivering an implant to a patient including an intravascular delivery catheter 300. According to one embodiment of the invention, the catheter 300 includes a connector, for example, a "Y" shaped connector 320. The connector 320 has a first connector port 310 for the syringe 200 and a second port for wire 302. The delivery system 400 also includes a syringe activated valve 100 of one of the valve types shown in FIGS. 2-8 and described above in the corresponding text. In one embodiment of the invention, the tip 204 of the syringe 200 is inserted into the first open end 104 of the valve 100 and secured with a standard luer lock as described above. In other embodiments, the valve is used in connection with other connector and other catheter types.

With continued reference to FIG. 9, if, in addition to injecting saline to remove air in the catheter 300, blood must be removed from the catheter lumen, a second syringe can be attached to the valve upon disconnecting the first syringe 200. Since the valve 100 automatically closes when the syringe 200 is removed, no air can enter into the catheter during the switch over from the first syringe to the second syringe. Operator errors are less likely to occur when utilizing the value described herein to flush an intravascular catheter compared to prior art devices, e.g., a three-way stopcock.

With continued reference to FIG. 9, as saline introduced under pressure from the syringe 200 by the operator through the passageway 114 in the valve 100, according to the invention described herein, into the delivery catheter 300, the air that is trapped in the catheter 300 is flushed from the distal end of the catheter. The syringe 200 can then be removed.

According to one embodiment of the invention, the valve 100, according to the invention described herein, is an integral part, i.e., manufactured as one piece with the connector or otherwise permanently joined as part of the delivery system 400. Alternatively, an existing delivery catheter can be retrofitted to replace prior art valves such as a three-way stopcock 306 with the valve 100 according to the invention. As a result, instead of manually opening the stopcock 306 to allow saline to pass through, a passageway is automatically opened up as the syringe 200 is attached to the valve 100.

While the invention has been particularly shown and described with reference to the preferred embodiments thereof, it will be understood by those skilled in the art that various changes in form and detail may be made therein without departing from the spirit and scope of the invention.

What is claimed is:

1. A delivery system for delivering an implant to an anatomical site in a patient, comprising:
   an intravascular catheter comprising a connector;
   a syringe-activated valve permanently joined to said connector, the syringe-activated valve comprising:
      a valve housing comprising a proximal end, a distal end, and an axial bore comprising a proximal cylindrical bore, a distal cylindrical bore, and a tapered shoulder positioned between said proximal cylindrical bore and said distal cylindrical bore;
      a substantially elongate, unitary sealing member enclosed by said valve housing, comprising an open position and a closed position, said sealing member slidably and axially disposed in said axial bore, said sealing member comprising a proximal cylindrical portion, a distal cylindrical portion, and an intermediate portion, said intermediate portion of said sealing member comprising a tapered shoulder, said shoulder interfacing with and cooperating with said tapered shoulder of the axial bore in the closed position, wherein a portion of the sealing member is longitudinally compressed when the sealing member moves from the closed position to the open position; and
      a backstop positioned in said distal bore distal to said distal portion of said sealing member and terminating proximal to said distal end of said valve housing, wherein said sealing member occludes said axial bore in the closed position and opens said axial bore in said open position; and
   a port for introducing the implant into the intravascular catheter for delivery to the anatomical site of the patient.

2. The syringe-activated valve of claim 1 wherein said backstop further comprises one or more perforations.

3. The syringe-activated valve of claim 1 wherein said backstop further comprises one or more gaps positioned between the backstop and the valve housing.

4. The syringe-activated valve of claim 2 wherein said backstop further comprises one or more projections extending from a proximal face of said backstop.

5. The syringe-activated valve of claim 4 wherein said projection comprises a cross-shape.

6. The syringe-activated valve of claim 4 wherein said one or more projections comprises a cone-shaped projection.

7. The syringe-activated valve of claim 4 wherein said one or more projections comprises a rectangular shaped projection.

8. The syringe-activated valve of claim 1 wherein said backstop comprises a disc-shape.

9. The syringe-activated valve of claim 1 wherein said backstop comprises a cylinder.

10. The syringe-activated valve of claim 1 wherein at least a portion of said sealing member is hollow.

11. The syringe-activated valve of claim 1 wherein the backstop is less resilient than the sealing member.

* * * * *